United States Patent [19]

Bockow et al.

[11] Patent Number: 5,912,006
[45] Date of Patent: *Jun. 15, 1999

[54] COMPOSITIONS AND METHODS FOR ALLEVIATING DISCOMFORTING MENSTRUAL PAIN

[75] Inventors: Barry I. Bockow, Seattle; Marc D. Erlitz, Kirkland, both of Wash.

[73] Assignee: EBOC, Inc., Seattle, Wash.

[*] Notice: This patent issued on a continued prosecution application filed under 37 CFR 1.53(d), and is subject to the twenty year patent term provisions of 35 U.S.C. 154(a)(2).

[21] Appl. No.: 08/704,819

[22] Filed: Aug. 28, 1996

[51] Int. Cl.⁶ ...................................... A61F 13/02
[52] U.S. Cl. .......................... 424/431; 424/430; 424/432; 424/433; 514/560
[58] Field of Search ..................... 424/431, 430, 424/432, 433; 514/560

[56] References Cited

U.S. PATENT DOCUMENTS

| 3,948,254 | 4/1976 | Zaffaroni | 128/127 |
| 4,601,714 | 7/1986 | Burnhill | 604/286 |
| 4,758,592 | 7/1988 | Horrobin | 514/549 |
| 5,273,521 | 12/1993 | Peiler | 604/13 |
| 5,409,925 | 4/1995 | Bockow | 514/560 |
| 5,703,066 | 12/1997 | Ottow | 514/173 |

OTHER PUBLICATIONS

Webster's New World Dictionary, V. Neufeldt, Ed. in Chief, Third College Edition, 1988. p. 1358.

*Primary Examiner*—D. Gabrielle Brouillette
*Attorney, Agent, or Firm*—Seed and Berry LLP

[57] ABSTRACT

There is disclosed a composition and method for reducing or alleviating the discomforting symptoms associate with menstruation, particularly menstrual pain. The composition is administered by topical or local administration to the uterus or vaginal tissues of a women in need thereof, and contains an omega fatty acid in combination with a cyclo-oxygenase inhibitor. Preferred omega fatty acids include docosahexaenoic acid and eicosapentaenoic acid, and preferred cyclo-oxygenase inhibitors include, ibuprophen, acetylsalicylic acid and salicylic acid. The composition may further include pharmaceutically acceptable carriers or diluents, and may be locally applied via intracervical or intrauterine application, or may be topically applied to the skin of the lower abdomen.

13 Claims, No Drawings

COMPOSITIONS AND METHODS FOR ALLEVIATING DISCOMFORTING MENSTRUAL PAIN

TECHNICAL FIELD

The present invention relates generally to compositions and methods for reducing or alleviating discomforting symptoms such as pain associated with menstruation.

BACKGROUND OF THE INVENTION

Virtually all menses subsequent to ovulation are associated with some pelvic discomfort, if only for the first few hours of bleeding. Such discomfort is due to myometrial contraction, which is an essential part of the menstrual cycle. While some discomfort and/or pain is normally associated with myometrial contraction, in some women the pain can become quite severe. Discomfort may also be present in the days preceding onset of menstruation.

Dysmenorrhea refers to excessive and often incapacitating pain at the time of menstruation. While various physiological factors can cause such pain (such as congenital uterovaginal malformation, pelvic infection, tumor, endometriosis, and other pelvic pathology), often no discernible cause for the pain can be identified. In such cases, it is believed that dysmenorrhea is likely caused by an exaggeration of the biochemical events leading to the synthesis of prostaglandin and related uterotonic metabolites and their action on the myometrium, and/or by an alteration in the women's response to the genuine discomfort of myometrial contraction.

Treatment of dysmenorrhea is typically accomplished by rest and local application of heat. In more severe cases, analgesics and sedatives are sometimes prescribed. Prostaglandin inhibitors may also be helpful, but often have systemic side effects. In cases were the episodes are recurrent and the degree of incapacity significant, a low-dose oral contraception therapy is often used (such as a combination of estrogen and progestin). Such therapy is believed to reduce the amount of prostaglandin precursors present in the endometrium at the end of the menstrual cycle and decrease the volume of blood lost during menses, thus reducing myometrial contractions.

While a limited number of techniques are presently available for reducing the discomforting symptoms associated with menses, such as pain, there is a need in the art for additional and improved compositions and methods for this purpose. The present invention fulfills these needs and provides further related advantages.

SUMMARY OF THE INVENTION

Briefly stated, the present invention discloses methods and compositions for reducing or alleviating the discomforting symptoms associated with menstruation, particularly menstrual pain. This is accomplished by topical or local administration of a composition of this invention to the uterus and/or vaginal tissues of a women in need thereof. Such compositions contain therapeutically effective amounts of an omega fatty acid and a cyclo-oxygenase inhibitor, and may optionally contain one or more acceptable carriers and/or diluents.

In one embodiment, a method for reducing or alleviating pain associated with menses is disclosed. Such method includes topical or local administration of a composition of this invention to a women in need thereof.

In another embodiment, a method for reducing or alleviating the discomforting symptoms associated with premenstrual syndrome is disclosed. In this method, a composition of the present invention is topically or locally administered to a women in need thereof prior to the onset of menstruation.

In still another embodiment, an intravaginal or intracervical device is disclosed for delivery of the composition of this invention. In a preferred embodiment, the device is a tampon and the composition is associated therewith for administration.

These and other aspects of this invention will become evident upon reference to the following detailed description.

DETAILED DESCRIPTION OF THE INVENTION

The present invention is generally directed to compositions which reduce or alleviate the discomforting symptoms associated with menses, or the onset thereof, as well as methods relating to the administration of such compositions. The compositions of the present invention contain both an omega fatty acid and a cyclo-oxygenase inhibitor.

Although not intending to be limited to the following theory, it is believed that the compositions of the present invention effectively modulate the syntheses of prostaglandins and leukotrienes, through interference with the cyclo-oxygenase and lipoxygenase pathways, respectively. For example, omega-3 fatty acids competitively inhibit the utilization of arachidonic acid in both cyclo-oxygenase and lipoxygenase pathways, and the cyclo-oxygenase inhibitor further inactivates the enzyme required for prostaglandin synthesis. The net effect of this combination renders the cyclo-oxygenase pathway and prostaglandin synthesis largely inoperative.

Prostaglandins are produced biosynthetically throughout the body. Prostaglandins are derived from enzymatic action on a common substrate, arachidonic acid. The first step in prostaglandin synthesis is the oxygenation of arachidonic acid by the enzyme cyclo-oxygenase. The oxygenated prostaglandin precursors are subject to further enzymatic processes which provide the various members of the prostaglandin family, including prostaglandin E2. Closely related in structure and function to the prostaglandins are a family of compounds known as leukotrienes. Leukotrienes are also derived from arachidonic acid metabolism, but through the lipoxygenase pathway. Like prostaglandins, leukotrienes enhance smooth muscle contraction.

Arachidonic acid is an essential fatty acid consisting of twenty carbon atoms and containing four carbon-carbon double bonds. By virtue of the position of carbon-carbon double bond at the methyl (omega) end of the hydrocarbon chain, it is classified as an omega-6 fatty acid. As discussed in greater detail below, a closely related family of fatty acids are the omega-3 fatty acids. In addition to double bond position, omega-6 and omega-3 fatty acids may also be distinguished by their origins. The precursors to these fatty acids are derived from plants which are in turn further metabolized in animals to provide the long chain polyunsaturated acids. Omega-6 fatty acids may be found predominantly in land animals, while omega-3 fatty acids are abundant in fish.

Oral administration of omega fatty acids has limited effectiveness and suffers from several drawbacks. Fatty acids that are taken orally are subject to gastrointestinal absorption and metabolism. In order to achieve delivery of effective quantities of fatty acids to the uterus, large quantities must be administered. To compensate for the reduction of active compound reaching the targeted organ, increased dosages of fatty acids are required. In addition, oral administration of fatty acids is not tissue specific and the dosage is distributed throughout the body. Because these omega fatty acids affect biological processes beyond prostaglandin synthesis, side effects associated with oral administration have been observed. For example, omega fatty acids are known to interfere with normal platelet function, and oral administration generally results in the increased danger of bleeding (Rogers et al., Atherosclerosis 63:137–43, 1987). The effect of omega fatty acids on platelet function also adversely affects capillary fragility. The increased dosages necessary for effective reduction or alleviation of menstrual symptoms, such as pain, serves to exacerbate the side effects due to interference with platelet function.

In addition to reducing or alleviating pain associated with menstruation, the compositions of this invention may also serve to reduce or alleviate other discomforting symptoms, such cramping, fluid retention, bloating, peripheral edema and/or emotional irritability.

Fatty acids are a class of organic compounds that are characterized by a long hydrocarbon chain terminating with a carboxylic acid group. Fatty acids have a carboxyl end and a methyl (i.e., "omega") end. Omega-3 fatty acids are a family of unsaturated fatty acids where the unsaturated carbon most distant from the carboxyl group is the third carbon from the methyl terminus. In general, omega-3 fatty acids have the following general formula:

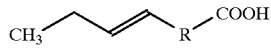

where R is a saturated or unsaturated, substituted or unsubstituted, branched or straight chain alkyl having from 1 to 20 carbon atoms. Preferably, R is an unsaturated straight chain alkyl having from 13 to 17 carbon atoms (i.e., an omega-3 fatty acid having from 18 to 22 total carbon atoms), and containing 2–6 carbon-carbon double bonds. In a particularly preferred embodiment, the omega-3 fatty acids of this invention contain 20 carbon atoms with 5 carbon-carbon double bonds, or 22 total carbon atoms with 6 total carbon-carbon double bonds, including (but not limited to) docosahexaenoic acid and eicosapentaenoic acid:

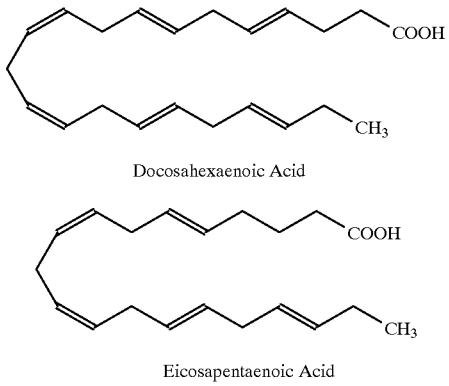

Docosahexaenoic Acid

Eicosapentaenoic Acid

Similarly, omega-6 fatty acids are a family of unsaturated fatty acids where the unsaturated carbon most distant from the carboxyl group is the sixth carbon from the methyl terminus. In general, omega-6 fatty acids have the following general formula:

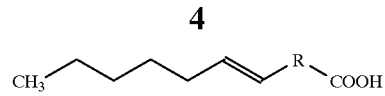

where R is a saturated or unsaturated, substituted or unsubstituted, branched or straight chain alkyl having from 1 to 20 carbon atoms.

While the omega fatty acids of this invention include both omega-3 and omega-6 fatty acids, in one embodiment omega-3 fatty acids are preferred.

The omega fatty acids of this invention are present in the composition in an amount sufficient to reduce or alleviate the discomforting symptoms associated with, or the onset of, menstration, particularly menstrual pain, when topically or locally administered in combination with a cyclo-oxygenase inhibitor. A single omega fatty acid may be employed (such as a single omega-6 fatty acid or, preferably, a single omega-3 fatty acid), or a mixture of two or more different omega fatty acids may be used (such as a mixture of two or more omega-3 fatty acids, or a mixture of one or more omega-3 fatty acids with one or more omega-6 fatty acids).

Cyclo-oxygenase inhibitors of the present invention include any compound which effectively inhibits cyclo-oxygenase, including (but not limited to) acetylating and non-acetylating inhibitors. Cyclo-oxygenase inhibitors which acetylate cyclo-oxygenase (i.e., "acetylating inhibitors") include (but are not limited to) acetylsalicylic acid (aspirin) and salicylsalicylic acid, as well as salts thereof. Cyclo-oxygenase inhibitors which do not acetylate cyclo-oxygenase (i.e., "non-acetylating inhibitors") include (but are not limited to) salicylates, such as salicylic acid, trilisate, and disalcid, and salts thereof. Other cyclo-oxygenase inhibitors include naproxen, piroxicam, indomethacin, sulindac, meclofenamate, diflunisal, tolmetin, phenylbutazone, ibuprof en, oxaprozin, etodolac, fenoprofen, ketoprofen and nabumetome.

The cyclo-oxygenase inhibitors of the present invention are present in the composition in an amount sufficient to reduce or alleviate the discomforting symptoms associated with, or the onset of, menstruation, particularly menstrual pain, when topically or locally administered in combination with an omega fatty acid. A single cyclo-oxygenase inhibitor may be employed, or a mixture of two or more different cyclo-oxygenase inhibitors may be used.

The compositions of the present invention may also contain additional optional ingredients including, but not limited to, vitamins E and A. Vitamin E is believed to prevent oxidation of the omega fatty acid of the composition, while vitamin A is believed to enhance adsorption of the same.

For purposes of local or topical administration, the compositions of the present invention may be formulated in any suitable manner, including (but not limited to) solutions, creams, oils, gels and vaginal suppositories, or applied in association with any suitable intravaginal or intracervical device, such as a tampon, sponge, diaphram or membrane (with or without a pessary). Suitable formulations contain effective amounts of both an omega fatty acid and a cyclo-oxygenase inhibitor, and may optionally contain one or more pharmaceutically acceptable carriers or diluents.

Tampons used for selective expulsion or delivery of medicaments and other materials into the vaginal cavity are well known, and may be used in the practice of this invention (see, e.g., U.S. Pat. Nos. 5,273,521, 4,309,997 and 4,318,405; each of which are incorporated herein by reference). Suitable tampons typically contain an absorbent material, and a composition of this invention may be inserted into the vaginal cavity followed by the tampon to prevent leakage. Alternatively, a composition of this invention may be impregnated onto or encapsulated within a tampon or other suitable applicator for delivery purposes. (See, e.g., U.S. Pat. No. 5,299,581; which is incorporated herein by reference.)

Other devices, such as that disclosed in U.S. Pat. No. 5,299,581 (incorporated herein by reference), may be used in conjunction with tampons and provide a means for administering a composition of this invention that otherwise might leak out. Additional delivery devices include those disclosed in U.S. Pat. No. 5,527,534 (incorporated herein by reference). In that patent, a sterile, vaginal sponge delivery system is disclosed suitable for the sustained release of a composition of this invention. Such sponges can be conveniently inserted and removed by the user without compromising the dosage and without waste or mess, and are advantages when the composition of this invention is administered to reduce or alleviate the discomforting symptoms of premenstrual syndrome prior to the onset of menses.

The compositions of this invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include (but are not limited to) emulsifying agents such as non-ionic ethoxylated and nonethoxylated surfactants, fatty alcohols, fatty acids, organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, hydrophilic beeswax derivatives, hydrocarbon oils (such as palm oil, coconut oil, and mineral oil), cocoa butter waxes, silicon oils, pH balancers and cellulose derivatives. One skilled in this art may further formulate the omega fatty acid and cyclo-oxygenase inhibitor in an appropriate manner, and in accordance with accepted practices, such as those disclosed in *Remington's Pharmaceutical Sciences*, Gennaro, Ed., Mack Publishing Co., Easton, Pa. 1990 (which is incorporated herein by reference in its entirety).

As mentioned above, the omega fatty acid and cyclo-oxygenase inhibitor is present in the composition in an amount sufficient to reduce or alleviate the discomforting symptoms associated with menses, particularly menstrual pain, when locally or topically applied. Formulated for local or topical application, the omega fatty acid is preferably present in an amount ranging from 1% to 90% by weight (based on the total weight of the formulation), more preferably from 10% to 80% by weight, and most preferably from 20% to 60% by weight. Similarly, the cyclo-oxygenase inhibitor is preferably present in an amount ranging from 0.1% to 20% by weight, more preferably from 1% to 10% by weight, and most preferably from 1% to 5% by weight.

The compositions of the present invention are administered by topical or local application (in contrast to systemic avenues, such as oral administration). For example, the compositions may be administered locally to the uterus via intravaginal or intracervical application. In one embodiment, the composition may be administered in association with a tampon. Compositions administered in this manner will diffuse into the uterus. Alternatively, the compositions of this invention may be applied to the surface of the lower abdomen, and diffuse through the skin to the uterus. Topical administration in this manner may be enhanced through the use of ultrasound or iontophoresis, or a combination of the two.

The topical/local nature of the administration of the compositions of the present invention provide advantages over existing systemic (including oral) administration. In particular, topical and local administration provides for rapid and increased delivery of the active omega fatty acid and cyclo-oxygenase inhibitor. The method of administration is therefore significantly more selective than oral administration and, as a result, smaller dosages of the active components are required. Furthermore, since the methods of administration of the present invention are specific to the uterus, the side effects of increased bleeding and capillary fragility associated with oral administration of omega fatty acids are also substantially reduced.

The following examples are provided for purposes of illustration, not by way of limitation.

EXAMPLES

Example 1

Representative Formulations

The following Formulations I, II and III are representative formulations containing the composition of the present invention for topical or local administration. to a women in need thereof as a cervical gel or vaginal suppository:

| Formulation I (cervical gel) | % by weight |
| --- | --- |
| Eicosapentaenoic acid | 40 |
| Docosahexaenoic acid | 5 |
| Ibuprophen | 3 |
| Vitamins E & A | 2 |
| Gel base | 50 |

| Formulation II (vaginal suppository) | % by weight |
| --- | --- |
| Eicosapentaenoic acid | 42 |
| Docosahexaenoic acid | 7 |
| Ibuprophen | 3 |
| Vitamins E & A | 5 |
| Suppository base | 43 |

| Formulation III (vaginal suppository) | % by weight |
| --- | --- |
| Eicosapentaenoic acid | 42 |
| Docosahexaenoic acid | 7 |
| Ibuprophen | 3 |
| Suppository base | 48 |

Example 2

Intravaginal Administration

A composition of this invention, such as the formulations of Example 1, may be delivered via a suitable applicator by techniques known in this field, such as a tampon applicator or other intravaginal device (see, e.g., the applicators and/or devices disclosed in U.S. Pat. Nos. 5,273,521, 5,299,581 and 5,527,534).

Example 3

Administration of Composition for Reducing or Alleviating Menstrual Pain

The following example illustrates the administration of a representative composition of the present invention to a woman suffering from dysmenorrhea.

Specifically, a 35 year-old women suffers from intense menstrual cramps, with or without contractions. They are so severe that she typically looses 1–3 days of work each month. Previously, she has taken potent. analgesics, including narcotics and oral antiinflammatories. However, these have caused undesirable side-effects, including gastritis, nausea, fluid retention and drowsiness.

A composition of this invention is administered by a tampon applicator as disclosed above in Example 2, not to exceed 6 times per day. She rapidly experiences a marked reduction in both the intensity and frequency of her painful cramps, and no longer finds it necessary to miss work due to the same.

From the foregoing, it will be appreciated that, although specific embodiments of the invention have been described herein for purposes of illustration, various modifications may be made without departing from the spirit and scope of the invention. Accordingly, the invention is not limited except as by the appended claims.

We claim:

1. A method for reducing or alleviating uterine or vaginal pain associated with or the onset of menstruation, comprising topically or locally administering to the uterus or vaginal tissue of a menstruating woman in need thereof an effective amount of a composition comprising an omega fatty acid and a cyclo-oxygenase inhibitor, wherein the woman is not suffering from endometriosis.

2. The method of claim 1 wherein the composition is administered in the form of a gel, cream or lotion.

3. The method of claim 1 wherein the composition is administered in the form of a vaginal suppository.

4. The method of claim 1 wherein the composition is administered in association with an intravaginal device.

5. The method of claim 4 wherein the intravaginal device is a tampon.

6. The method of claim 4 wherein the intravaginal device is a vaginal sponge.

7. The method of claim 1 wherein the composition is administered to the surface of the lower abdomen.

8. The method of claim 1 wherein the omega fatty acid of the composition has at least one of the following structures:

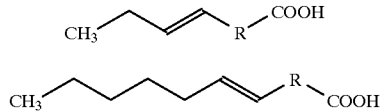

wherein R is a saturated or unsaturated, substituted or unsubstituted, branched or straight chain alkyl having from 1 to 20 carbon atoms.

9. The method of claim 1 wherein the omega fatty acid is eicosapentaenoic acid.

10. The method of claim 1 wherein the omega fatty acid is docosahexaenoic acid.

11. The method of claim 1 wherein the cyclo-oxygenase inhibitor is an acetylating inhibitor selected from acetylsalicylic acid, salicylsalicylic acid, and salts thereof.

12. The method of claim 1 wherein the cyclo-oxygenase inhibitor is a non-acetylating inhibitor selected from salicylic acid, trilisate, disalcid, and salts thereof.

13. The method of claim 1 wherein the cyclo-oxygenase inhibitor is selected from naproxen, piroxicam, indomethacin, sulindac, meclofenamate, diflunisal, tolmetin, ibuprofen, oxaprozin, etodolac, fenoprofen, ketoprofen and nabumetone.

* * * * *